United States Patent
Bai et al.

(10) Patent No.: US 9,059,135 B2
(45) Date of Patent: Jun. 16, 2015

(54) NANOCHANNEL PROCESS AND STRUCTURE FOR BIO-DETECTION

(71) Applicant: International Business Machines Corporation, Armonk, NY (US)

(72) Inventors: Jingwei Bai, Elmsford, NY (US); Evan G. Colgan, Chestnut Ridge, NY (US); Christopher V. Jahnes, Upper Saddle River, NJ (US); Stanislav Polonsky, Putnam Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 53 days.

(21) Appl. No.: 13/969,595

(22) Filed: Aug. 18, 2013

(65) Prior Publication Data

US 2014/0370637 A1    Dec. 18, 2014

Related U.S. Application Data

(63) Continuation of application No. 13/920,226, filed on Jun. 18, 2013, now Pat. No. 8,901,621.

(51) Int. Cl.
| | |
|---|---|
| *G01N 27/403* | (2006.01) |
| *H01L 29/40* | (2006.01) |
| *G01N 27/414* | (2006.01) |
| *H01L 21/283* | (2006.01) |
| *H01L 21/8238* | (2006.01) |

(52) U.S. Cl.
CPC .......... *H01L 29/401* (2013.01); *G01N 27/4148* (2013.01); *G01N 27/403* (2013.01); *H01L 21/283* (2013.01); *H01L 21/823871* (2013.01)

(58) Field of Classification Search
None
See application file for complete search history.

(56) References Cited

U.S. PATENT DOCUMENTS

| | | | |
|---|---|---|---|
| 6,582,987 B2 | 6/2003 | Jun et al. | 438/49 |
| 6,995,439 B1 | 2/2006 | Hill et al. | 257/396 |
| 7,171,975 B2 | 2/2007 | Moon et al. | 137/15.01 |
| 7,510,982 B1 | 3/2009 | Draeger et al. | 438/783 |
| 7,670,770 B2 | 3/2010 | Chou et al. | 435/6.12 |
| 8,129,286 B2 | 3/2012 | Edelstein et al. | 438/733 |
| 2007/0122313 A1* | 5/2007 | Li et al. | 422/100 |
| 2010/0267158 A1 | 10/2010 | Chou et al. | 436/94 |
| 2011/0006367 A1 | 1/2011 | Fuller et al. | 257/347 |
| 2012/0256281 A1 | 10/2012 | Harrer et al. | 257/414 |

FOREIGN PATENT DOCUMENTS

KR    101105309    5/2009    ............ G01N 33/50

OTHER PUBLICATIONS

Schoch, Han, and Renaud, Transport phenomena in nanofluidics, Rev. Mod. Phys., vol. 80, pp. 839-883 (2008).

* cited by examiner

*Primary Examiner* — Kyoung Lee
(74) *Attorney, Agent, or Firm* — Ido Tuchman; Louis J. Percello

(57) ABSTRACT

Nanochannel sensors and methods for constructing nanochannel sensors. An example method includes forming a sacrificial line on an insulating layer, forming a dielectric layer, etching a pair of electrode trenches, forming a pair of electrodes, and removing the sacrificial line to form a nanochannel. The dielectric layer may be formed on insulating layer and around the sacrificial line. The pair of electrode trenches may be etched in the dielectric layer on opposite sides of the sacrificial line. The pair of electrodes may be formed by filling the electrode trenches with electrode material. The sacrificial line may be removed by forming a nanochannel between the at least one pair of electrodes.

9 Claims, 19 Drawing Sheets

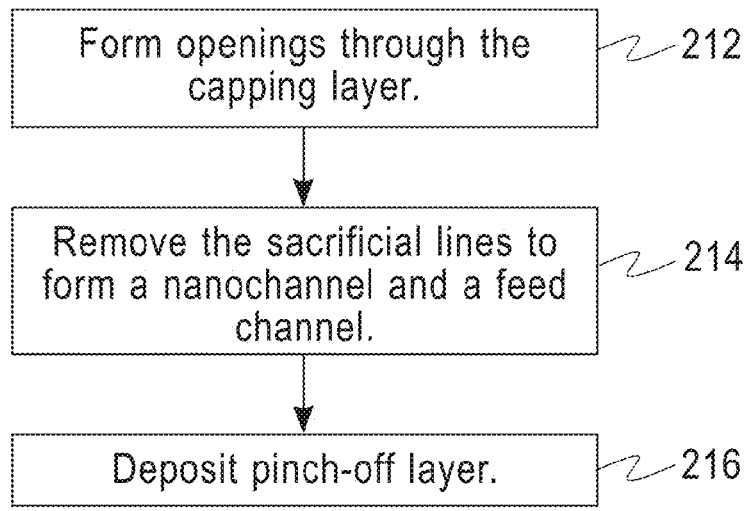
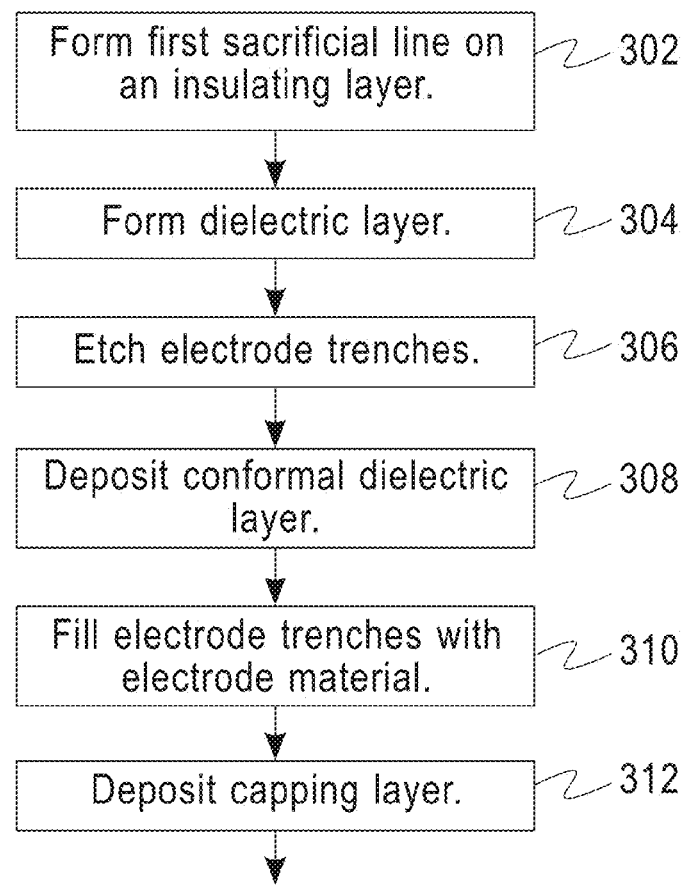
FIG. 2B
FIG. 3A

US 9,059,135 B2

NANOCHANNEL PROCESS AND STRUCTURE FOR BIO-DETECTION

CROSS-REFERENCE TO RELATED APPLICATIONS

This application claims priority under 35 U.S.C. §120 to U.S. patent application Ser. No. 13/920,226 filed Jun. 18, 2013, the entire text of which is specifically incorporated by reference herein.

BACKGROUND

This invention relates to molecular sensors, and more particularly to nanochannel sensors and methods for constructing nanochannel sensors.

Biosensors may be constructed by integrating nanochannels into complementary metal-oxide-semiconductor (CMOS) chips. These nanochannels may exhibit diameters of a few microns for cell and bacteria sensing. They may also range from tens of nanometers to a fraction of a nanometer in diameter for virus and biological macromolecule sensing.

Pairs of electrodes may line biosensor nanochannels and may be used to detect such objects as cells, cell fragments, bacteria, viruses and biological macromolecules in the nanochannels. The electrodes detect the objects in the solutions flowing within the nanochannels. The electrode pairs may also be used to generate electric fields in and around nanochannels. The electric fields may be used to manipulate charged objects in the solution within the nanochannels, for example aligning molecules with the length of the nanochannel, holding molecules in places, or moving molecules along the nanochannels.

BRIEF SUMMARY

Accordingly, one example aspect of the present invention is a nanochannel sensor which includes a substrate, a dielectric layer, a nanochannel, a feed channel, and a pair of electrodes. The dielectric layer may be formed over the substrate. The nanochannel and the feed channel may be formed in the dielectric layer. The feed channel may include a bottom portion and a top portion. The top portion of the feed channel may have a greater cross-sectional width than the bottom portion of the feed channel. The pair of electrodes may be positioned on opposing sides of the nanochannel.

Another example aspect of the present invention is a nanochannel sensor which includes a substrate, a dielectric layer, a nanochannel, a feed channel, a pair of electrodes, and a second dielectric layer. The first dielectric layer may be formed over the substrate. The nanochannel and the feed channel may be formed in the dielectric layer. The pair of electrodes may be positioned on opposing sides of the nanochannel. The capping layer may cover the feed channel. The capping layer may also define a plurality of openings through the second dielectric layer leading to the feed channel.

Yet another example aspect of the present invention is a method of aligning electrodes to a nanochannel sensor including forming a sacrificial line on an insulating layer, forming a dielectric layer, etching a pair of electrode trenches, forming a pair of electrodes, and removing the sacrificial line to form a nanochannel. The first dielectric layer may be formed on the substrate and around the sacrificial line. The pair of electrode trenches may be etched in the first dielectric layer on opposite sides of the sacrificial line. The pair of electrodes may be formed by filling the electrode trenches with electrode material. The sacrificial line may be removed by forming a nanochannel between the at least one pair of electrodes.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIGS. 2A and 2B show a continuous flow diagram illustrating a first example method for aligning electrodes to a nanochannel sensor in accordance with another embodiment of the invention.

FIGS. 3A and 3B show a continuous flow diagram illustrating second example method of aligning electrodes to a nanochannel sensor, in accordance with yet another embodiment of the invention.

DETAILED DESCRIPTION

Figure 1A:
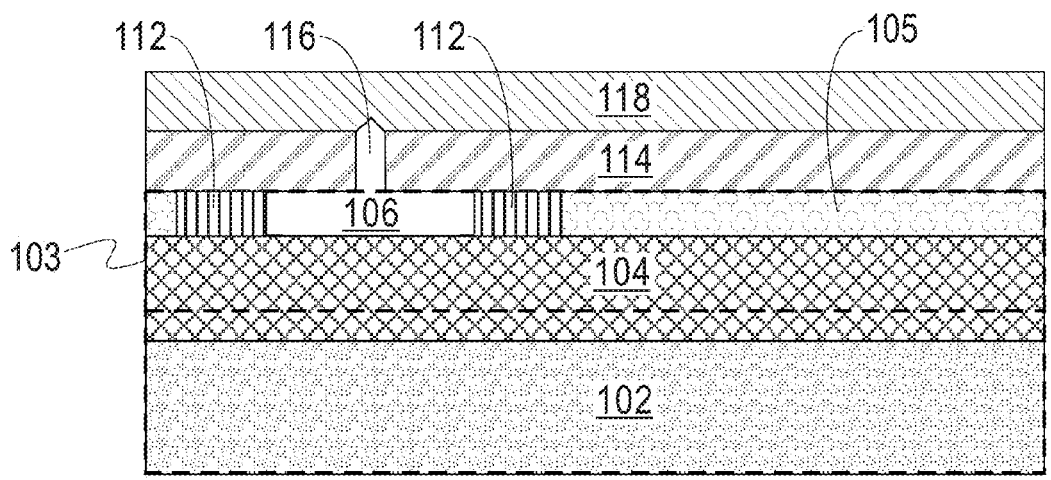
FIGS. 1A, 1B, and 1C show a nanochannel sensor in accordance with one embodiment of the invention.

The present invention is described with reference to embodiments of the invention. Throughout the description of the invention reference is made to FIGS. 1A-19C. When referring to the figures, like structures and elements shown throughout are indicated with like reference numerals.

Figure 1B:
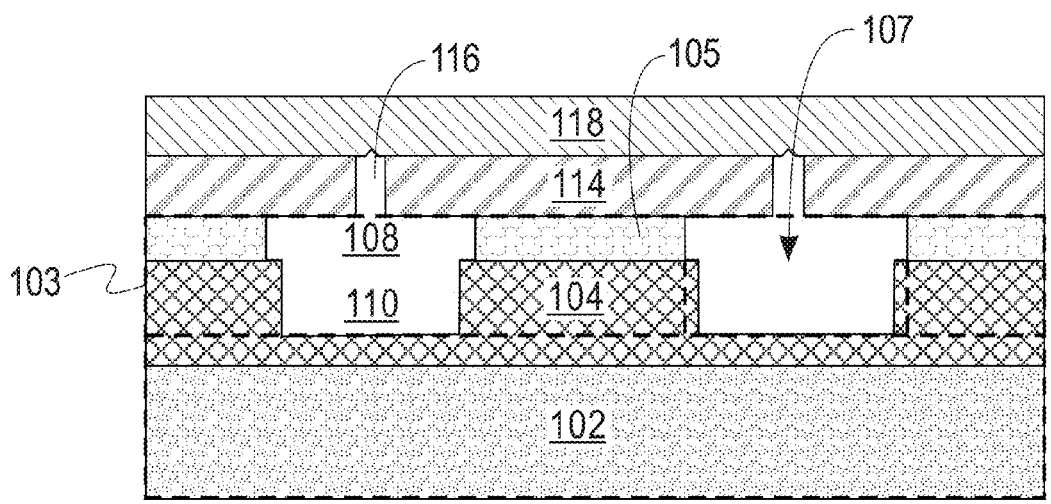
Figure 1C:
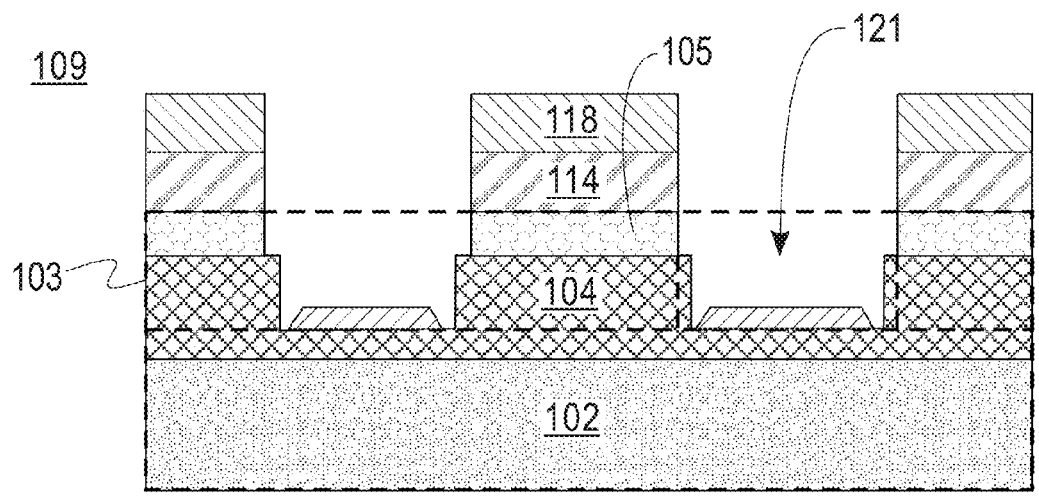

FIGS. 1A, 1B, and 1C show a nanochannel sensor comprising a nanochannel sensor region 100, a feed channel region 101, and a port region 109 according to one embodiment of the invention. The nanochannel sensor region 100 includes a substrate 102, a dielectric layer 103, a nanochannel 106 and a pair of electrodes 112. The nanochannel sensor region 100 may also include a capping layer 114. The feed channel region 101 includes a feed channel 107 formed within the dielectric layer 103. The port region 109 includes a fluid inlet/outlet port 121 formed within the dielectric layers 103, 114 and 118.

The dielectric layer 103 may be formed over the substrate 102. The dielectric layer 103 may be an insulating film. For example, the dielectric layer 103 may contain silicon dioxide. The substrate 102 may also contain a layer of dielectric below the dielectric layer 103 and the feed channel 107. The nanochannel 106 may be formed in the dielectric layer 103. The feed channel 107 may also be formed in the dielectric layer 103. The feed channel 107 may include a bottom portion 110 and a top portion 108, with the top portion 108 having a greater cross-sectional width than the bottom portion 110. The top portion 108 of the feed channel 107 and the nanochannel 106 may also have a smaller cross-sectional height than the bottom portion 110 of the feed channel 107. The top portion 108 may also extend beyond the edges of the bottom portion 110. The nanochannel 106 may be of the same height as the top portion 108 of the feed channel 107, and formed from the same sacrificial layer as the top portion 108 of the feed channel 107.

According to one embodiment of the invention, the dielectric layer 103 may include a bottom dielectric layer 104 and a top dielectric layer 105. The nanochannel 106 may be formed in the top dielectric layer 105. The top portion 108 of the feed channel 107 may be formed in the top dielectric layer 105, and the bottom portion 110 of the feed channel 107 may be formed in the bottom dielectric layer 104.

The pair of electrodes 112 may be positioned on opposing sides of the nanochannel 106. Electrodes 112 may contain a thin palladium (Pd) layer, a titanium nitride (TiN) diffusion barrier, followed by a copper layer. The electrodes 112 may be formed in the top dielectric layer 105.

According to one embodiment of the invention, the nanochannel sensor may also include a capping layer 114 over the dielectric layer 103. The capping layer 114 may cover the nanochannel 106, the feed channel 107, and the electrodes 112. The capping layer 114 may also define a plurality of openings 116 through the capping layer 114 leading to the feed channel 107 and/or the nanochannel 106. The capping layer 114 may also be a thin insulator layer.

According to another embodiment of the invention, the nanochannel sensor may also include a conformal dielectric layer 120 between the nanochannel 106 and the electrodes 112. Furthermore, the conformal dielectric layer 120 may contain aluminum oxide or hafnium oxide. A pinch-off layer 118 of dielectric material may "pinch-off" or seal the plurality of openings 116 in the capping layer 114. The pinch-off layer maybe a thin non-conformal dielectric.

According to yet another embodiment of the invention, the port region 109 shown in FIG. 1C, which includes fluid inlet or outlet port 121 maybe formed simultaneously and by the same processes used to form the nanochannel channel sensor and feed channel regions where opening are provided through the bottom dielectric layer 104, top dielectric layer 105, and capping layer 114. The fluid inlet port 121 is connected to (i.e., fluid communication with) the feed channel region 101, which is connected to the nanochannel channel sensor region 100, which is connected to another feed channel region, and which is connected to the fluid outlet port 121. To insure that the feed channels are not sealed where they connect to the port region, a non-conformal dielectric layer is used for the pinch-off layer. Note that the pinch-off layer is deposited at the bottom of the fluid inlet or outlet ports, 121, so the layer thickness should be less than the height of the feed channel (i.e., sum of the thickness of the bottom dielectric layer 104 and top dielectric layer 105).

Figure 2A:
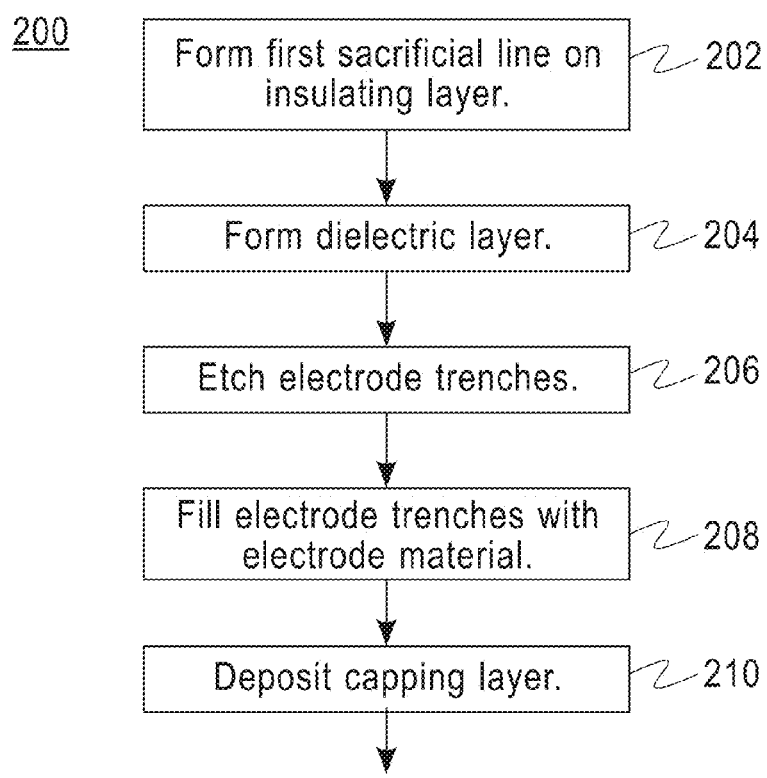
Figure 20:
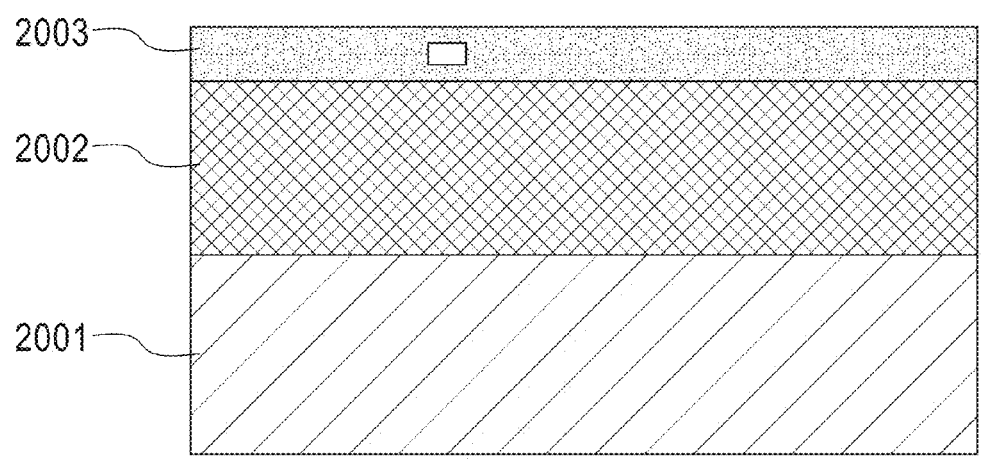
FIG. 20 shows a cross-sectional view of a nanochannel sensor integrated with the back end of line (BEOL) wiring layers on a CMOS chip.

According to yet another embodiment of the invention, the substrate 102 may include an insulator layer, such as silicon dioxide ($SiO_2$), deposited on a wafer, such as a silicon wafer. The substrate 102 may also be a portion of a silicon-on-insulator (SOI) wafer. FIGS. 2A and 2B show a first example method 200 of aligning electrodes to a nanochannel sensor, in accordance with one embodiment of the invention. In one embodiment of the invention, the method 200 is integrated with a back end of line (BEOL) chip fabrication process. For example, FIG. 20 shows a CMOS substrate 2001 containing the active electronic devices, carrying the back end of line (BEOL) 2002 wiring layers that interconnect the active devices, and the nanochannel sensor 2003. The wiring layers provide electrical connections between the nanochannel sensor 2003 and the active devices on the CMOS substrate 2001.

Returning to FIG. 2, the method 200 may include forming a sacrificial line on a substrate 202, forming a dielectric layer 204, etching one pair of electrode trenches 206, forming one pair of electrodes 208, depositing a capping layer 210, forming openings through the capping layer 212, removing the sacrificial lines to form a nanochannel and a feed channel 214, and depositing a pinch-off layer 216

Figure 4A:
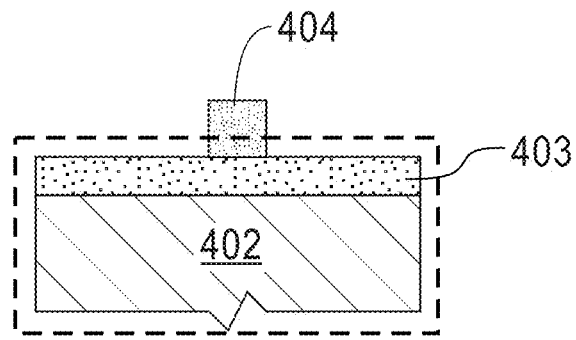
FIGS. 4A and 4B show a cross-sectional view and a top view, respectively, of a sacrificial line deposition step, in accordance with the first example method for aligning electrodes to a nanochannel sensor.
Figure 4B:
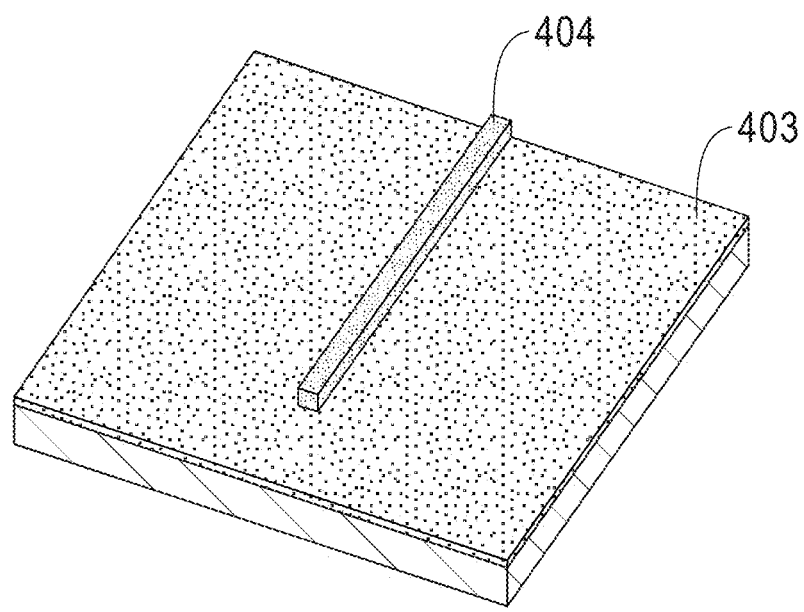

The method 200 involves a sacrificial line formation step 202, as shown on FIGS. 4A and 4B. At the sacrificial line formation step 202, a sacrificial line 404 is deposited on an insulating layer 403. The insulating layer 403 may include silicon dioxide ($SiO_2$), deposited on a wafer, such a silicon wafer. The insulating layer may also be part of a silicon-on-insulator (SOI) wafer, in which case the sacrificial line 404 may be formed by etching the thin silicon layer of the wafer above the insulator, resulting in the structures shown in FIGS. 4A and 4B.

According to one embodiment of the invention, the sacrificial line 404 may contain sacrificial line material such as polysilicon, amorphous silicon, single crystalline silicon, or germanium. The dimensions of the sacrificial line 404 may be varied by changing the thickness and the line width of the sacrificial line materials. The sacrificial line may be formed from a thin film of the sacrificial line material. Furthermore, the sacrificial line 404 may be patterned using a reactive ion etch (RIE) process, conventional lithography, electron beam technology, or a sidewall transfer process. Following patterning, the sacrificial line material may also be partially oxidized to reduce the dimensions of the material.

Figure 5A:
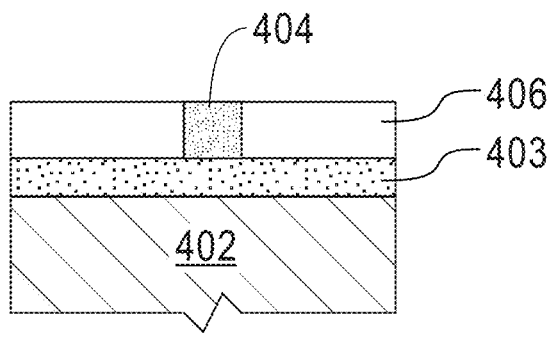
FIGS. 5A and 5B show a cross-sectional view and a top view, respectively, of a dielectric layer formation and planarization steps, in accordance with the first example method for aligning electrodes to a nanochannel sensor.
Figure 5B:
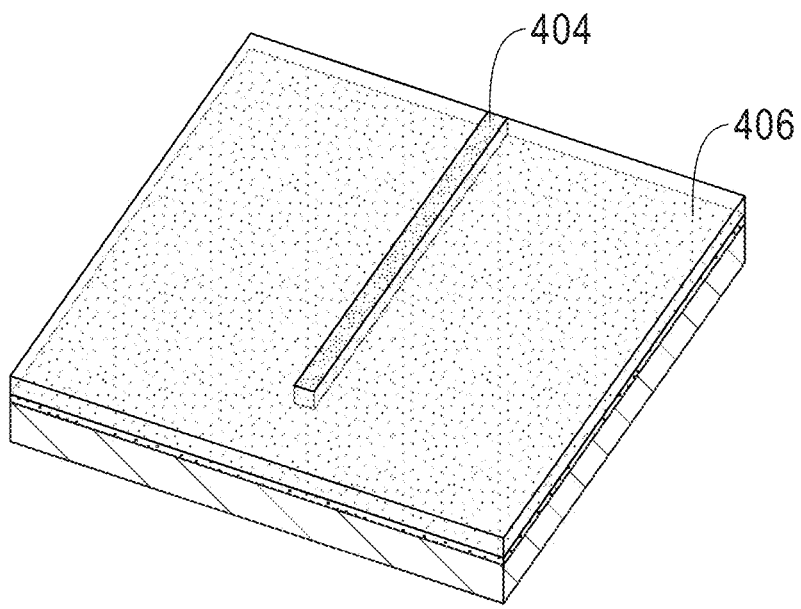

Returning to FIGS. 2A-2B, after the sacrificial line formation step 202, the method 200 proceeds to a dielectric layer formation step 204, as shown on FIGS. 5A and 5B. At the dielectric layer formation step 204, the first dielectric layer 406 is formed on the insulating layer 403 and around the sacrificial line 404. The dielectric layer 406 may be an insulating film. It may also contain silicon dioxide. The dielectric layer may be formed by using plasma enhanced chemical vapor deposition (PECVD) of an insulating material, followed by a chemical-mechanical polishing (CMP) step in order to planarize the material. The CMP step may stop at the top surface of the sacrificial line 404.

Figure 6A:
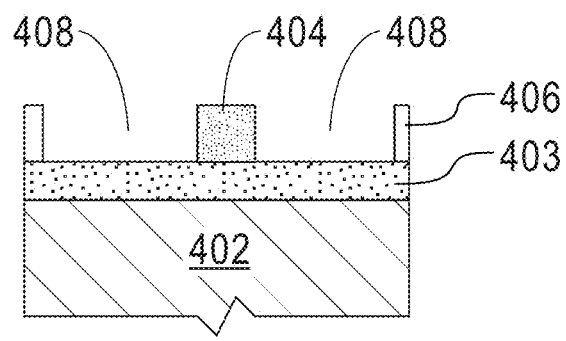
FIGS. 6A and 6B show a cross-sectional view and a top view, respectively, of an electrode trench etching step, in accordance with the first example method for aligning electrodes to a nanochannel sensor.
Figure 6B:
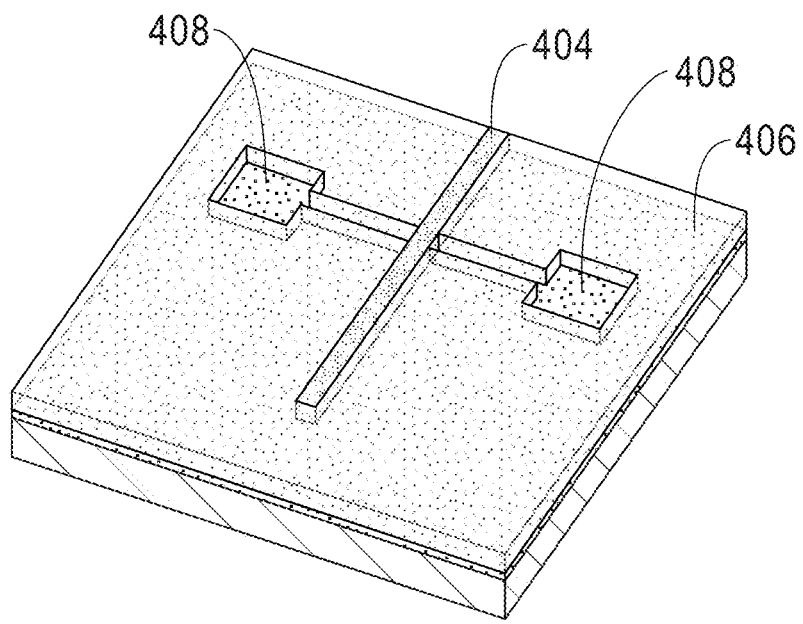
Figure 7A:
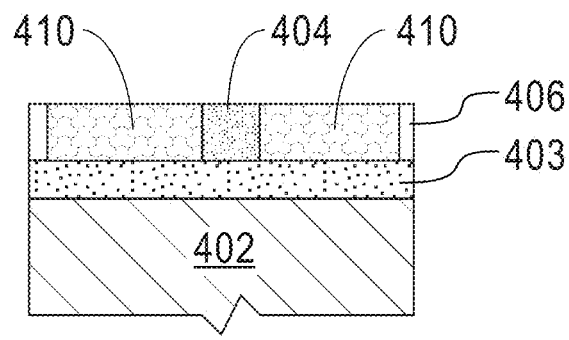
FIGS. 7A and 7B show a cross-sectional view and a top view, respectively, of an electrode formation step, in accordance with the first example method for aligning electrodes to a nanochannel sensor.
Figure 7B:
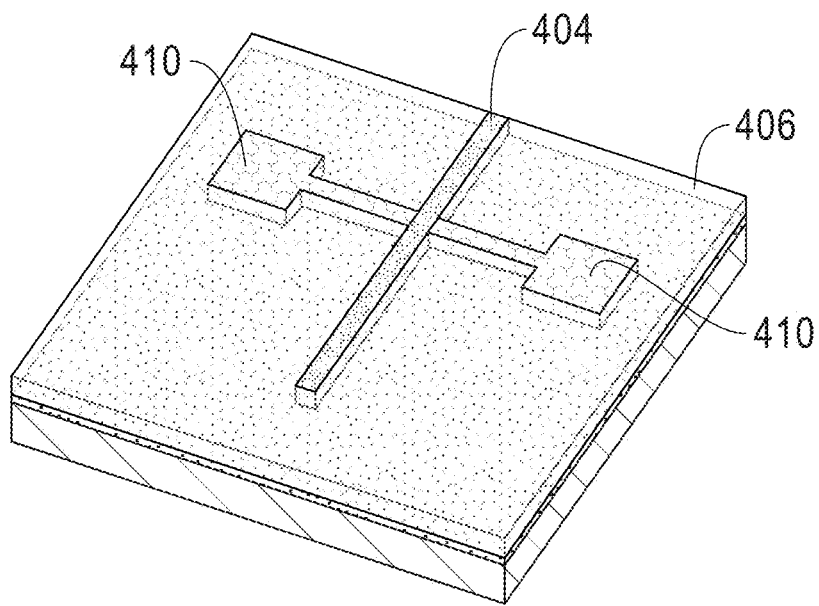

Returning to FIG. 2A-2B, after the dielectric layer formation step 204, the method 200 proceeds to an electrode trench etching step 206, as shown on FIGS. 6A and 6B. At the electrode trench etching step 206, at least one pair of electrode trenches 408 are etched in the dielectric layer 406 on opposite sides of the sacrificial line 404. The electrode trench etching step 206 may also involve etching the dielectric layer at a faster etch rate than etching the sacrificial line. A RIE process maybe used, for example, to form the trench.

The electrode trenches 408 may be perpendicular to the sacrificial line 404, and may be etched into the dielectric layer 406. The electrode trench etching step 206 may be accomplished with little or no etching of the sacrificial line 404. Furthermore, the depth of the trenches may be controlled by controlling the etch time, or by building an etch stop in the first dielectric layer 406, or below it. The electrode trench 406 may be etched into the insulating layer 403. Returning to FIGS. 2A-2B, after the electrode trench etching step 206, the method 200 proceeds to an electrode formation step 208, as shown on FIGS. 7A and 7B. At the electrode formation step 208, at least one pair of electrodes 410 are formed by filling the electrode trenches 408 with electrode material. CMP may be used to planarize the electrode material. The electrodes may include multiple layers. For example, sensing electrodes may contain a thin palladium (Pd) layer, a titanium nitride (TiN) diffusion barrier, followed by a copper layer. If Pd is used, an Ar sputtering process may be used to etch exposed Pd if it is not removed by CMP.

Figure 8A:
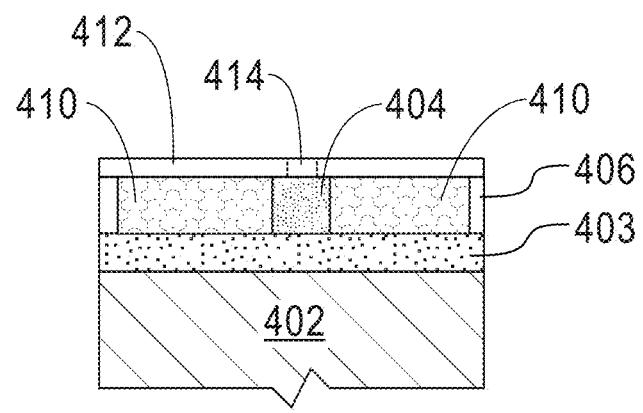
FIGS. 8A and 8B show a cross-sectional view and a top view, respectively, of a second dielectric layer formation step, and the formation of openings in the second dielectric layer, in accordance with the first example method for aligning electrodes to a nanochannel sensor.
Figure 8B:
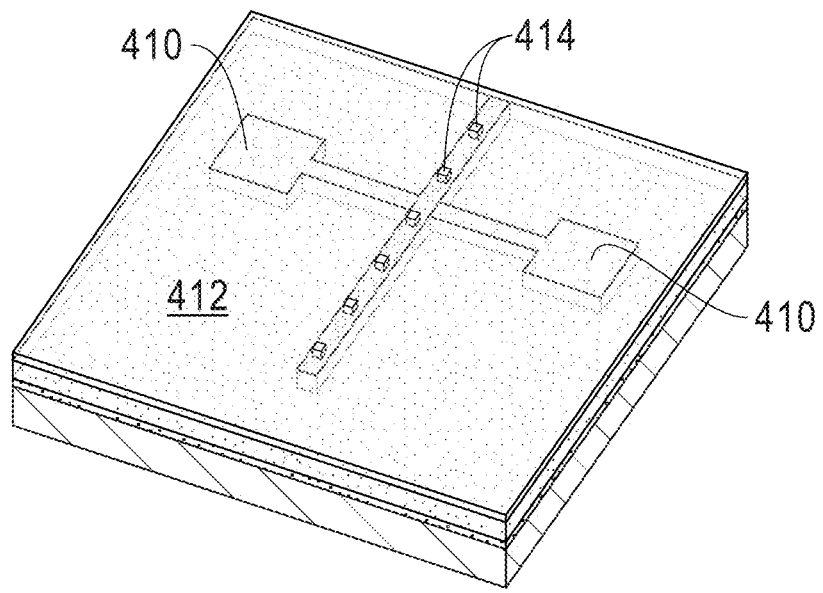

Returning to FIGS. 2A-2B, after the electrode formation step 208, the method 200 proceeds to a capping layer formation step 210, as shown on FIGS. 8A and 8B. At the capping layer formation step 210, a capping layer 412 is deposited. The capping layer 412 may cover the sacrificial line 404 and the electrodes 410. The second dielectric layer 412 may also be a thin insulator layer.

Returning to FIGS. 2A-2B, after the capping layer formation step 210, the method 200 proceeds to an opening etching step 212. At the opening etching step 212, a plurality of openings or holes 414 are formed through the capping layer 412. These openings 414 may lead to the sacrificial line 404 and expose the sacrificial line 404. Note that if the sacrificial line was partially oxidized, the openings or holes would be etched through the oxidized layer along with the capping layer 412 to expose the sacrificial line 404. The openings 414 are shown in FIGS. 8A and 8B.

Figure 9A:
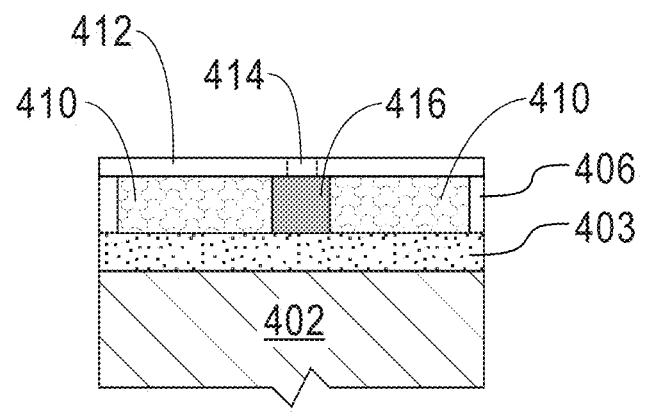
FIGS. 9A and 9B show a cross-sectional view and a top view, respectively, of a sacrificial line removal step, in accordance with the first example method for aligning electrodes to a nanochannel sensor.
Figure 9B:
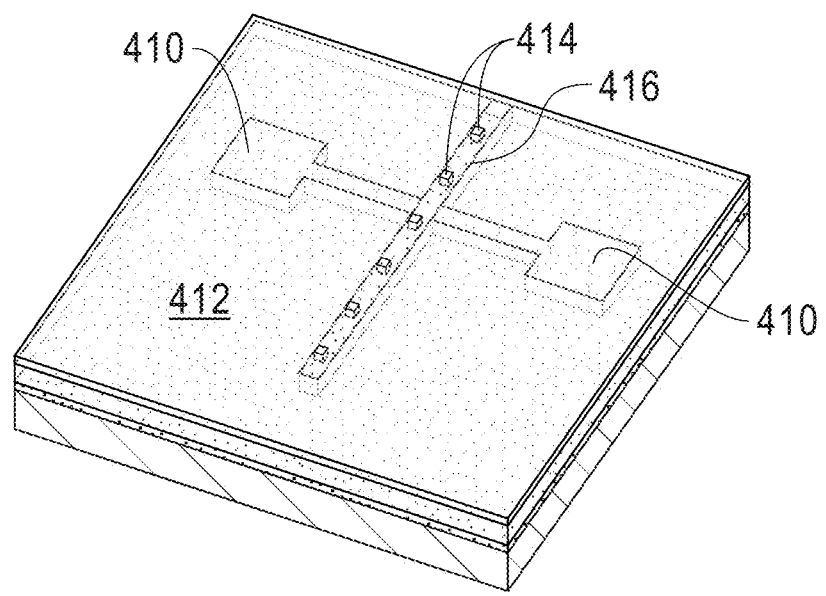

Returning to FIGS. 2A-2B, after the opening etching step 212, the method 200 proceeds to a sacrificial line removal step 214, as shown on FIGS. 9A and 9B. At the sacrificial line removal step 214, the sacrificial line 404 is removed in order to form a nanochannel 416 between the electrodes 410. The sacrificial line removal step 214 may include introducing Xenon Difluoride ($XeF_2$) to the sacrificial line 404 through the plurality of openings 414. $XeF_2$ may be introduced using a vapor phase etch process. The sacrificial line removal step 214 may involve minimal or no etching of components other than the sacrificial line 404.

According to one embodiment of the invention, the method 200 may also be used to form feed channels in addition to nanochannels 416. Feed channels and nanochannels 416 may form long, continuous channels and may be formed simultaneously using the first example method 200. Feed channels may include a bottom portion and a top portion. The top portion of the feed channel may have a greater width than the bottom portion. The top portion of the feed channel may also have a smaller height than the bottom portion of the feed channel. The overall cross-sectional area (i.e. height times width) of the bottom portion of the feed channel may be greater than the cross-sectional area of the top portion of the feed channel.

According to one embodiment of the invention, each pair of electrodes 410 is self-aligned on opposite sides of the nanochannel 416. The electrodes 410 may also be electrically isolated from the contents of nanochannel 416. The electrodes 410 may be in direct electrical contact with the nanochannel 416, for example, in Ohmic contact with the contents of the nanochannel 416.

Figure 10A:
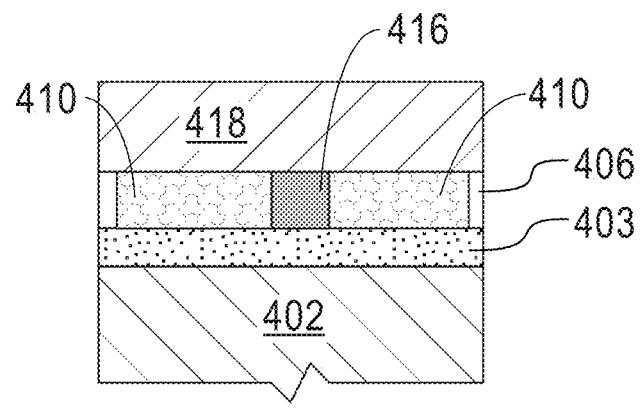
FIGS. 10A and 10B show a cross-sectional view and a top view, respectively, of a pinch-off step, in accordance with the first example method for aligning electrodes to a nanochannel sensor.
Figure 10B:
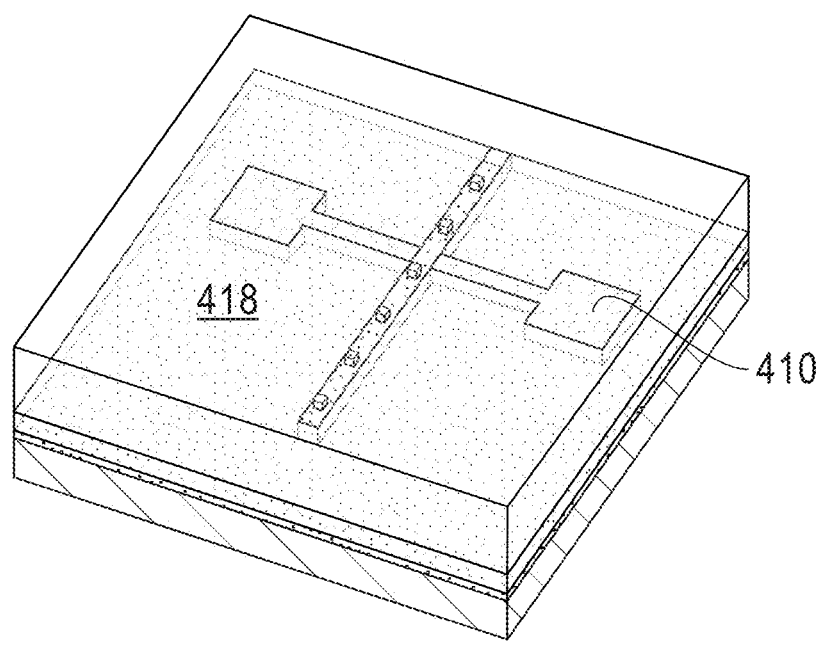

After the sacrificial line removal step 214, the method 200 may proceed to a pinch-off step 216, as shown on FIGS. 10A and 10B. At the pinch-off step, a pinch-off layer 418 is deposited on the capping layer 412. The pinch-off layer 418 may seal or "pinch off" the openings 414 leading to the sacrificial line 404. The pinch-off layer 418 may be a thin non-conformal insulator layer. The pinch-off step 216 may be a conventional microelectromechanical systems (MEMS) fabrication step.

Figure 11A:
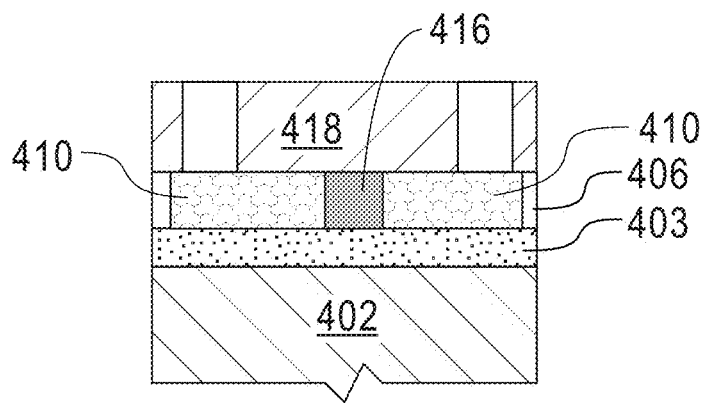
FIGS. 11A and 11B show a cross-sectional view and a top view, respectively, of inlet, outlet, and electrode exposure step, in accordance with the first example method for aligning electrodes to a nanochannel sensor.
Figure 11B:
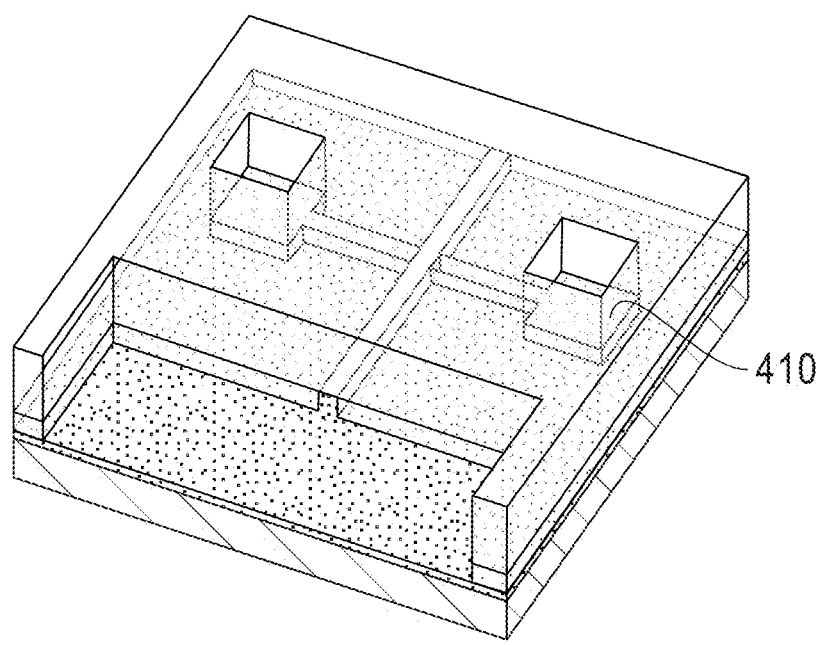

After the pinch-off step 216, the method 200 may proceed to etching steps for exposing inlet reservoirs, outlet reservoirs, and electrodes, as shown in FIGS. 11A and 11B. These etching steps may be performed using a RIE process. Any inlets and outlets may be connected to nanochannel. Inlets and outlets may also contain biasing electrodes.

According to one embodiment of the invention, the plurality of openings 414 leading to the sacrificial line may be located away from the sites designated for inlet and outlet reservoirs. Thus, during the sacrificial line removal step 214, removal of the sacrificial line 404 may be limited to the portions of the sacrificial line 404 away from the reservoirs. After initial removal of the sacrificial line, the etching steps for exposing inlet and outlet reservoirs may be selected to minimize etching of the surviving portions of the sacrificial line. Finally, the surviving portions of the sacrificial line may be removed, for example using vapor phase $XeF_2$, forming a completed nanochannel. The openings 414 may also connect to sections of the sacrificial line away from the nanochannel segments of the sacrificial line. For example, the openings may connect to the feed channel segments of the sacrificial line.

According to one embodiment of the invention, the completed nanochannel sensor constructed using the first example method 200 may be used to conduct impedance spectroscopy experiments.

Figure 3B:
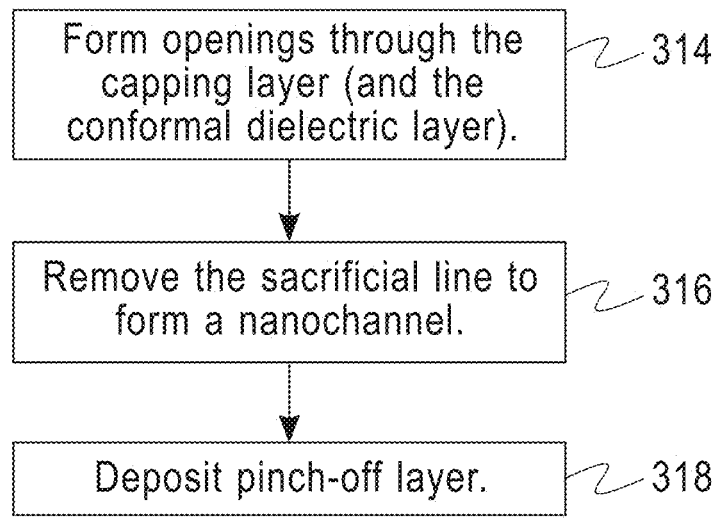

FIGS. 3A and 3B show a second example method 300 of aligning electrodes to a nanochannel sensor, in accordance with another embodiment of the invention. Many of the steps of the method 300 shown in FIGS. 3A and 3B are similar to the method shown in FIGS. 2A-2B.

The method 300 involves a sacrificial line formation step 302. At the sacrificial line formation step 302, a sacrificial line is formed on an insulating layer. After the sacrificial line formation step 302, the method 300 proceeds to a dielectric layer formation step 304.

At the dielectric layer formation step 304, a dielectric layer is formed on the substrate, around the sacrificial line, and planarized. After the dielectric layer formation step 304, the method 300 proceeds to an electrode trench etching step 306.

At the electrode trench etching step 306, at least one pair of electrode trenches are etched in the dielectric layer on opposite sides of the sacrificial line. After the electrode trench etching step 306, the method 200 proceeds to conformal dielectric layer deposition step 308.

At the conformal dielectric layer deposition step 308, a conformal high-k dielectric layer is deposited between the sacrificial line and the electrode trenches. The conformal high-k dielectric layer may be a thin film and may contain materials such as aluminum oxide or hafnium oxide. The conformal dielectric layer may be selected in order to allow etching during the opening etching step 314 but to minimize or prevent etching during the sacrificial line removal step 316. After the conformal dielectric layer deposition step 308, the method 300 proceeds to an electrode formation step 310.

At the electrode formation step 310, at least one pair of electrodes is formed by filling the electrode trenches with electrode material. CMP may be used to planarize the electrode material. The electrodes may include multiple layers. For example, the electrodes may contain a titanium nitride (TiN) diffusion barrier, followed by a copper layer. CMP may be used to planarize the electrode material. After the electrode formation step 310, the method 300 proceeds to a capping layer formation step 312.

At the capping layer formation step 312, a capping layer is deposited. The capping layer may cover the conformal dielectric layer over the sacrificial line 404, if it is not removed by the CMP process, and the electrodes. After the capping layer formation step 312, the method 300 proceeds to an opening etching step 314.

At the opening etching step 314, a plurality of openings are formed through the capping layer and leading to the sacrificial line. The openings may also be openings in the conformal dielectric layer. After the opening etching step 314, the method 300 proceeds to a sacrificial line removal step 316.

At the sacrificial line removal step 316, the sacrificial line is removed in order to form a nanochannel between the electrodes. The sacrificial line removal step may include Xenon Difluoride etching of the sacrificial line through the plurality of openings.

After the sacrificial line removal step 316, the method 300 may proceed to a pinch-off step 318. At the pinch-off step 318, a pinch-off layer is deposited on the capping layer. The pinch-off layer may seal or "pinch off" the openings leading to the sacrificial line. The pinch-off layer may be a thin non-conformal insulator layer. The pinch-off step may be a conventional MEMS fabrication step.

After the pinch-off step 318, the method 300 may proceed to etching steps for exposing electrodes contact pads. These etching steps may be performed using a RIE process. Any inlets and outlets may be connected to nanochannel. Inlets and outlets may also contain biasing electrodes.

According to one embodiment of the invention, the method 300 may also be used to form feed channels in addition to nanochannels. Feed channels and nanochannels may form long, continuous channels and may be formed simultaneously using the second example method 300. Feed channels may include a bottom portion and a top portion. The top portion of the feed channel may have a greater width than the bottom portion. The top portion of the feed channel may also have a smaller height than the bottom portion of the feed channel. The overall cross-sectional area (i.e. height times width) of the bottom portion of the feed channel may be greater than the cross-sectional area of the top portion of the feed channel.

According to one embodiment of the invention, the plurality of openings leading to the sacrificial line may be located away from the sites designated for inlet and outlet reservoirs. Thus, during the sacrificial line removal step 316, removal of the sacrificial line may be limited to the portions of the sacrificial line away from the reservoirs. After initial removal of the sacrificial line, the etching steps for exposing inlet and outlet reservoirs may be selected to minimize etching of the surviving portions of the sacrificial line. Finally, the surviving portions of the sacrificial line may be removed, for example using vapor phase $XeF_2$, forming a completed nanochannel. The openings may also connect to sections of the sacrificial line away from the nanochannel segments of the sacrificial line. For example, the openings may connect to the feed channel segments of the sacrificial line.

In a completed nanochannel sensor constructed according the second example method 300, electrodes may be used to create electric fields that have the ability to hold or move particles of interest within the nanochannel.

Figure 12:
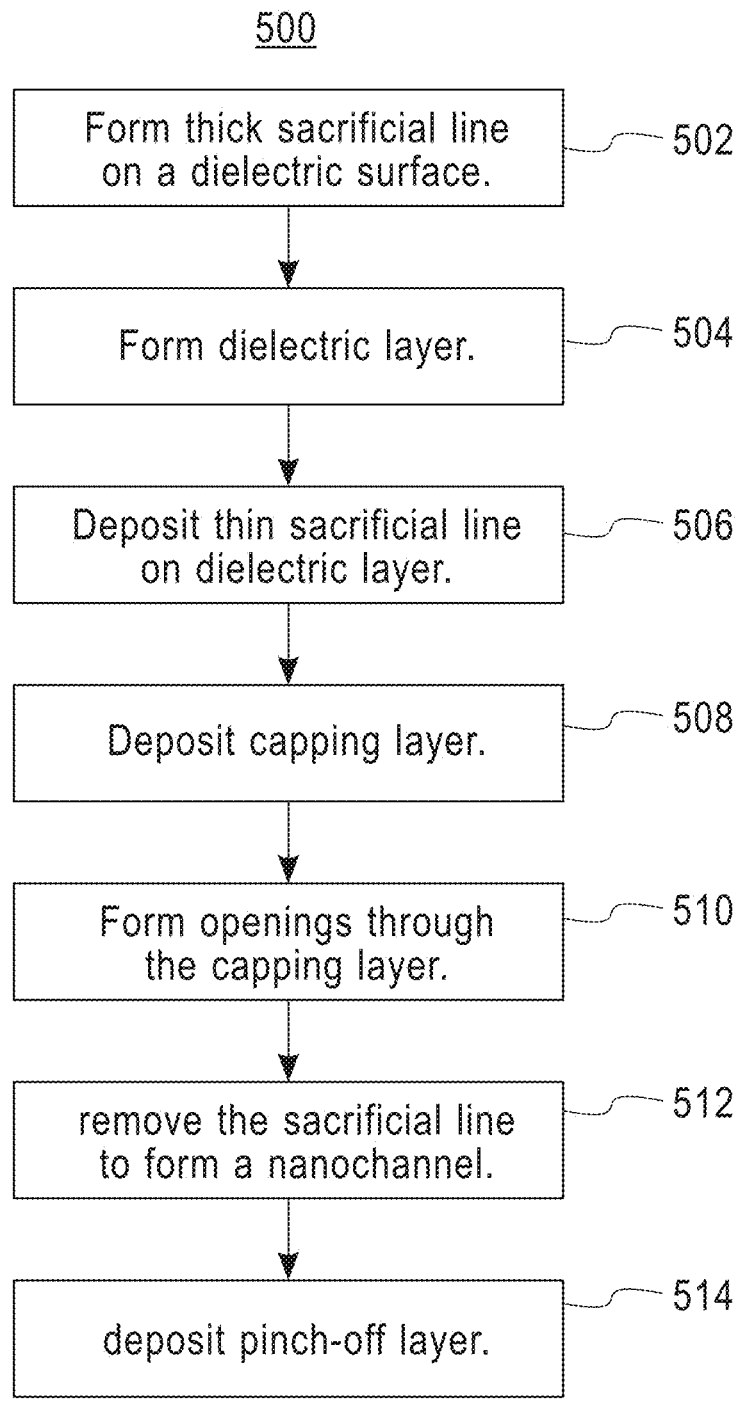
FIG. 12 shows flow diagram illustrating a third example method for constructing a nanochannel sensor, according to yet another embodiment of the invention.

FIG. 12 shows a third example method 500 for constructing a nanochannel sensor, according to yet another embodiment of the invention. Many of the steps of the method 500 shown in FIG. 12 are similar to the methods shown in FIGS. 2A, 2B, 3A and 3B.

Figure 13A:
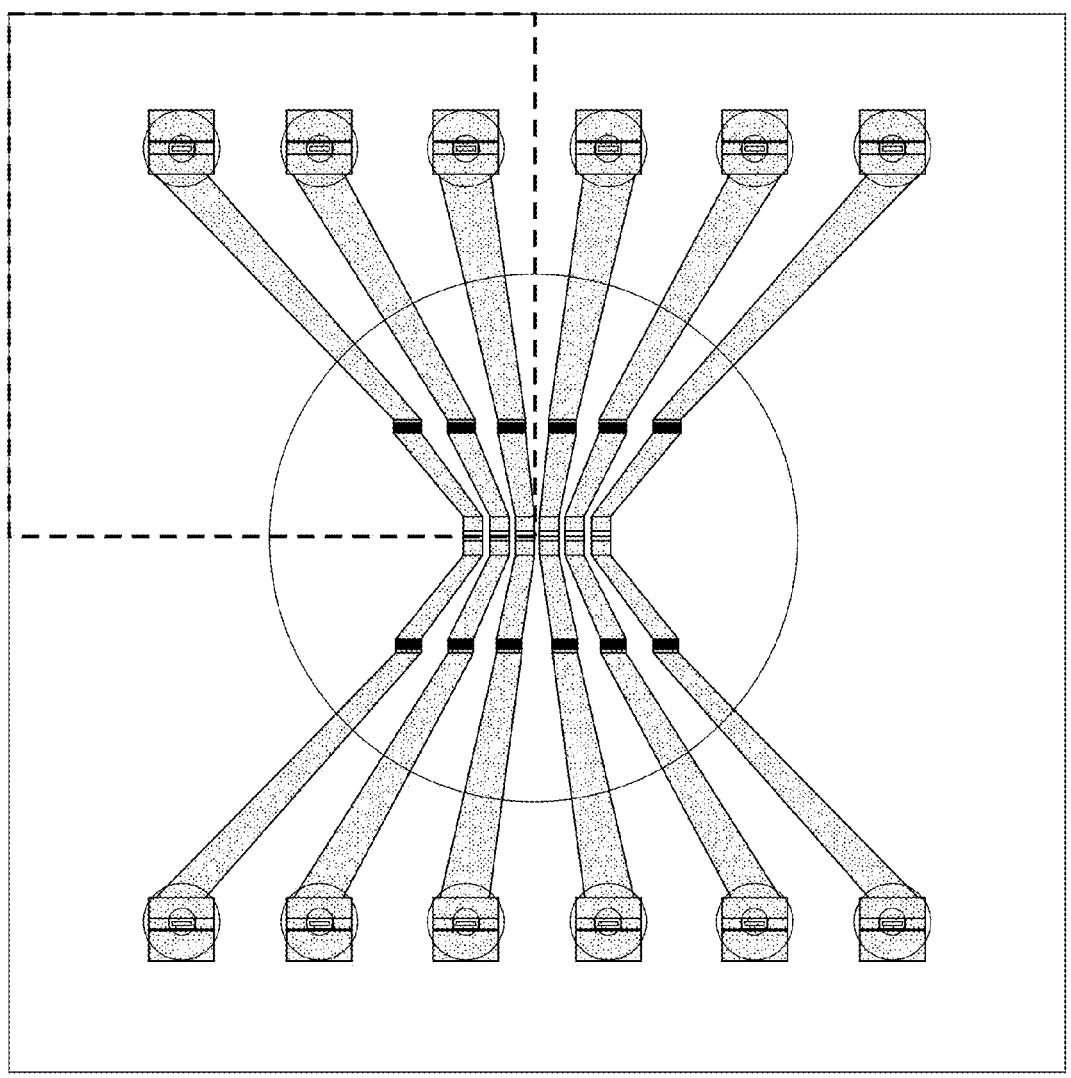
FIGS. 13A-13C show a nanochannel sensor including a fluid port region, feed channel region and a nanochannel region constructed according to the third example method.
Figure 13B:
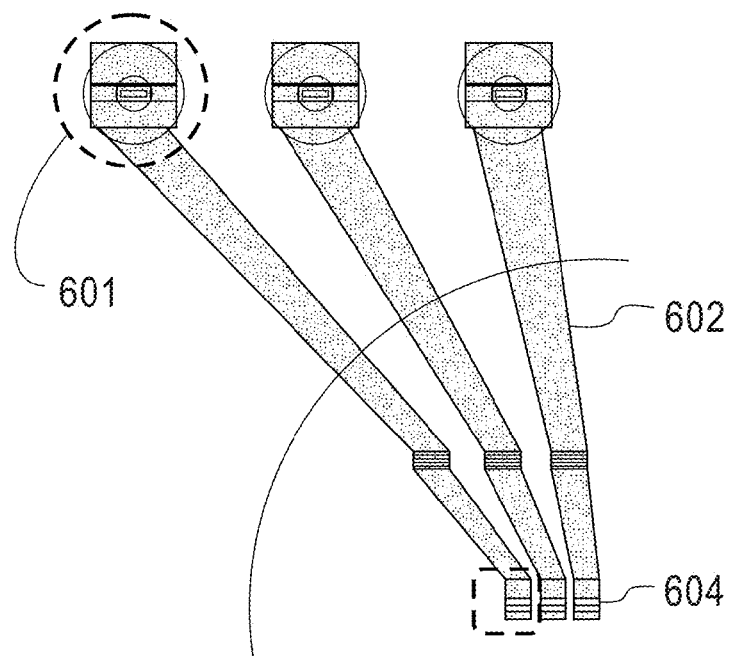
Figure 13C:
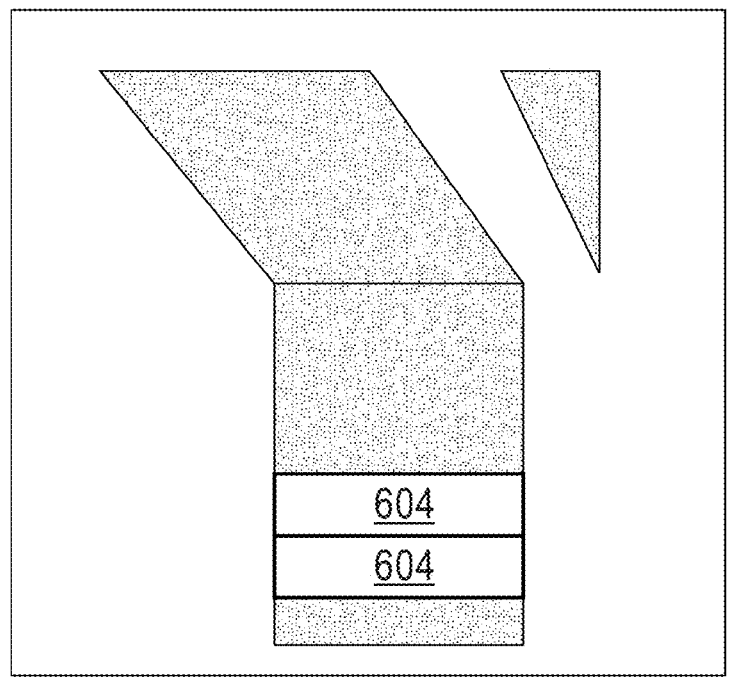

The method 500 involves constructing a nanochannel sensor 600 with a feed channel region 602 and a nanochannel region 604, as shown in FIGS. 13A-13C.

FIG. 13A shows an integrated nanochannel sensor 600 implemented in a 40×40 mm CMOS chip. FIG. 13B shows a portion of the integrated channel sensor 600, previously highlighted in FIG. 13A. FIG. 13B shows the fluid port regions 601, feed channel regions 602 and nanochannel regions 604 of the chip 600. FIG. 13C shows a portion of the integrated channel sensor, highlighted in FIG. 13B. Fluid generally flows in from one fluid port 601, through a feed channel region 602, through a nanochannel region 604. Fluid may flow out through a reverse path, through a second nanochannel region 604, through a second feed channel region 602, and out through a second fluid port 601. The feed channel region may also include a supporting mesh, possibly constructed of silicon oxide. The mesh may provide structural support to the feed channel region during fluid flow. The feed channels may have a much greater cross sectional area than the nanochannels. This may be accomplished by using an additional thick sacrificial layer in the feed channel region 602. To permit integration of the nanochannel sensor with the CMOS wiring (back end of line; BEOL) layers, the sacrificial lines maybe formed of amorphous silicon or other materials which can be deposited at temperatures of about 400° C. or less and etched by Xenon Difluoride. In this case, the substrate would contain the CMOS circuits and may also contain one or more of the BEOL wiring layers.

Figure 14A:
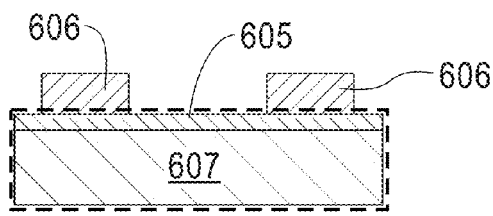
FIGS. 14A, 14B and 14C show cross-sectional views of the port region, nanochannel region and feed channel region, respectively, of a thick sacrificial line deposition step, in accordance with the third example method for constructing a nanochannel sensor.
Figure 14B:
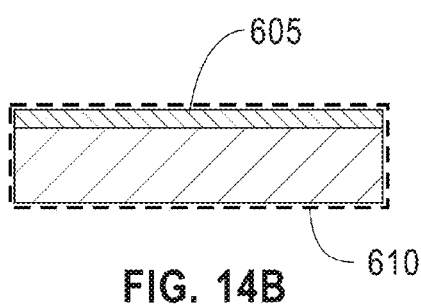
Figure 14C:
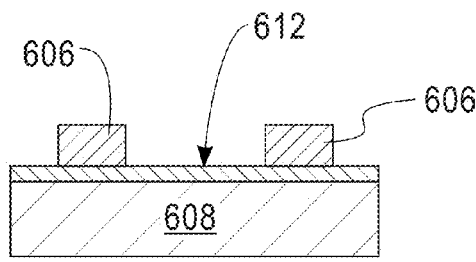

The method 500 begins with a thick sacrificial line formation step 502, as shown on FIGS. 14A-14C. At the thick sacrificial line formation step 502, one or more thick sacrificial lines 606 are formed on the feed channel region substrate 608 and the port region substrate 607. The substrates 607, 608, and 610 may contain an insulating layer 605 on the surface.

The thick sacrificial lines 606 may be formed from a thin film of the sacrificial line material. Furthermore, the thick sacrificial line 606 may be patterned using reactive ion etching (RIE), conventional lithography, electron beam technology, or a sidewall transfer process.

Figure 15A:
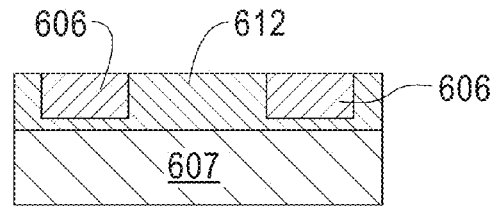
FIGS. 15A, 15B and 15C show cross-sectional views of the port region, nanochannel region and feed channel region, respectively, of a first dielectric layer formation and planarization steps, in accordance with the third example method for constructing a nanochannel sensor.
Figure 15B:
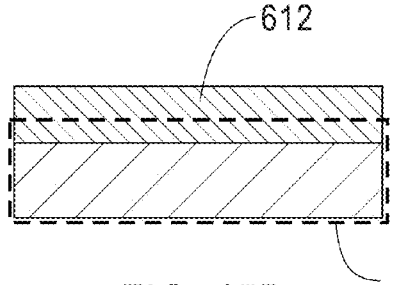
Figure 15C:
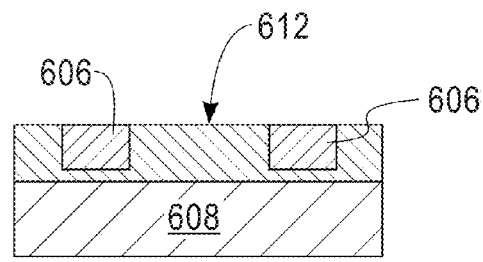

After the thick sacrificial line formation step 502, the method 500 proceeds to a dielectric layer formation step 504, as shown on FIGS. 15A-15C. At the dielectric layer formation step 504, a dielectric layer 612 is formed on the port region substrate 607, feed channel region substrate 608 and the nanochannel region substrate 610. The dielectric layer is also formed over the thick sacrificial line 606. Chemical-mechanical polishing (CMP) may then be used to planarize the first dielectric layer and expose the top surface of the thick sacrificial line 606. Those skilled in the art would recognize that additional thick sacrificial lines of progressively increasing width may be formed on top of the first thick line by repeating steps 502 and 504.

Figure 16A:
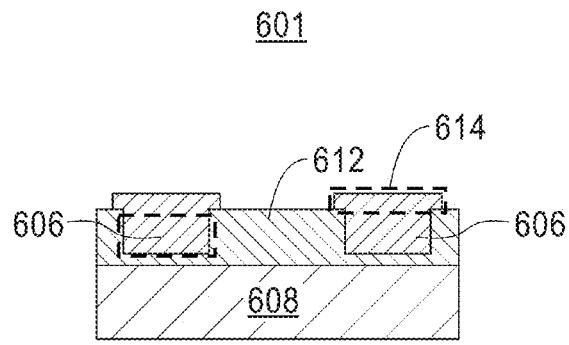
FIGS. 16A, 16B and 16C show cross-sectional views of the port region, nanochannel region and feed channel region, respectively, of a thin sacrificial line deposition step, in accordance with the third example method for constructing a nanochannel sensor.
Figure 16B:
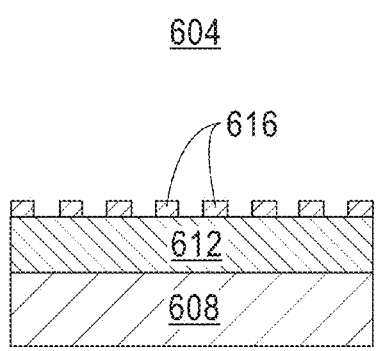
Figure 16C:
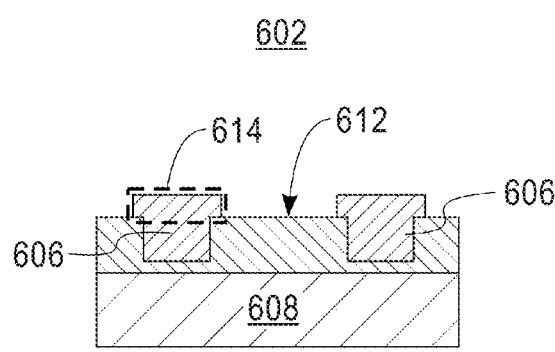

After the dielectric layer formation step 504, the method 500 proceeds to a thin sacrificial line deposition step 506, as shown in FIGS. 16A-16C. At the thin sacrificial line deposition step 506, thin layers of sacrificial lines 614 and 616 are deposited over the dielectric layer 612 or over the thick sacrificial lines 606. In the nanochannel region 604, thin, narrow sacrificial lines 616 are deposited over the first dielectric layer 612. In the port region 601 and feed channel region 602, thin, wide sacrificial lines 614 are deposited over both the dielectric layer 612 and the thick sacrificial line 606, and extend beyond the edges of the thick sacrificial lines 606.

The thin sacrificial lines 614 and 616 may have thinner cross sections than the thick sacrificial lines 606. The thin, wide sacrificial lines 614 may have a wider cross section than the thin, narrow sacrificial lines 616. The thin, wide sacrificial lines 614 may also have a wider cross section than the thick sacrificial lines 606 and extend beyond their edges.

According to one embodiment of the invention, the thin and thick sacrificial lines 606, 614 and 616 may contain sacrificial line material such as polysilicon, amorphous silicon, single crystalline silicon, germanium, tungsten, molybdenum, tantalum or tantalum nitride. The thin sacrificial lines 614 and 616 may be formed from a thin film of the sacrificial line material. Furthermore, the thin sacrificial lines 614 and 616 may be patterned using reactive ion etching (RIE), conventional lithography, electron beam technology, or a sidewall transfer process. Following patterning, the thin sacrificial line material may also be oxidized.

Figure 17A:
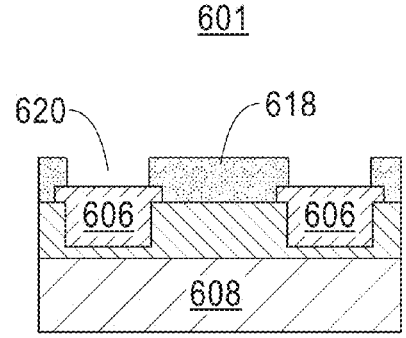
FIGS. 17A, 17B and 17C show cross-sectional views of the port region, nanochannel region and feed channel region, respectively, of a second dielectric layer formation step, in accordance with the third example method for constructing a nanochannel sensor.
Figure 17B:
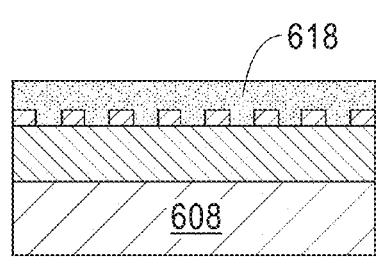
Figure 17C:
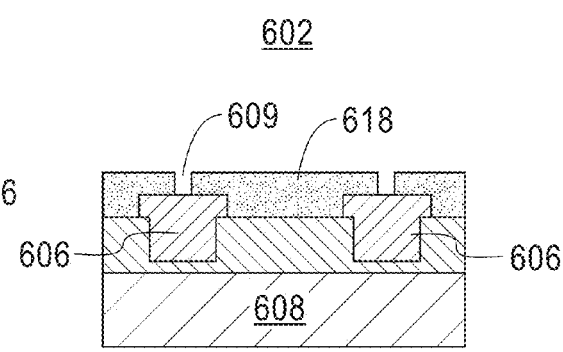

Returning to FIG. 12, after the thin sacrificial line deposition step 506, the method 500 proceeds to a capping layer formation step 508, as shown on FIGS. 17A-17C. At the second dielectric layer formation step 508, a capping layer 618 is deposited. The capping layer 618 may cover the thin sacrificial lines 614 and 616 and the dielectric layer 612. The capping layer 618 may also be a thin insulator layer. CMP may be used to planarize the surface of the second dielectric layer, possibly without removing enough material to expose the thin sacrificial lines.

After the capping layer formation step 508, the method 500 proceeds to an opening etching step 510. At the opening etching step 510, a plurality of openings or holes 609 and 620 are formed through the capping layer 618 in the feed channel region 602 and port region 601, respectively. These openings 609 and 620 may lead to and expose the thin, wide sacrificial lines 614, as shown on FIGS. 17A and 17C.

Figure 18A:
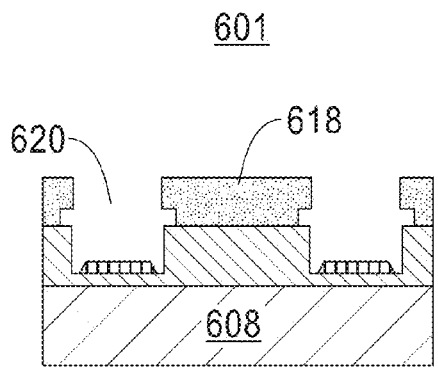
FIGS. 18A, 18B and 18C show cross-sectional views of the port region, nanochannel region and feed channel region, respectively, of a sacrificial line removal step, in accordance with the third example method for constructing a nanochannel sensor.
Figure 18B:
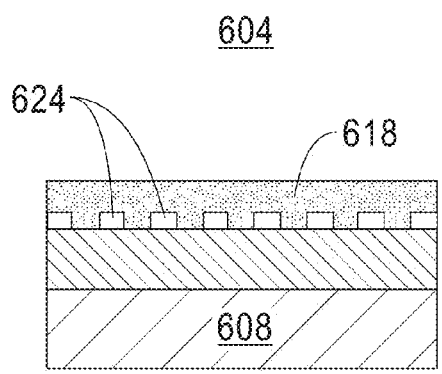
Figure 18C:
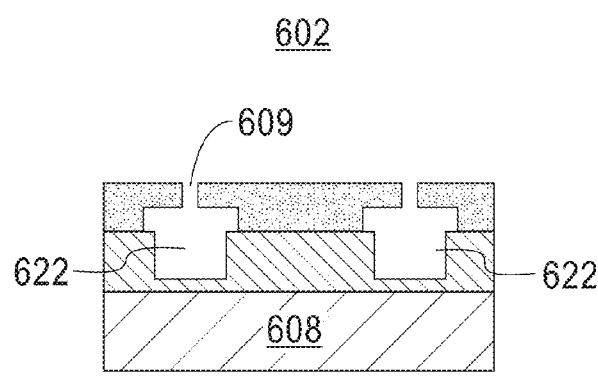

Returning to FIG. 12, after the opening etching step 510, the method 500 proceeds to a sacrificial line removal step 512, as shown on FIGS. 18A-18C. At the sacrificial line removal step 512, the sacrificial lines 606, 614, and 616 are removed in order to form the port 620, feed channels 622 and nanochannels 624. Removal of the thick sacrificial lines and the thin, wide sacrificial lines creates feed channels 622 and removal of the thin, narrow sacrificial lines creates nanochannels. The sacrificial line removal step 512 may include introducing Xenon Difluoride ($XeF_2$) to the sacrificial lines 606, 614, and 616 through the plurality of openings 620 and 609. $XeF_2$ may be introduced using a vapor phase etch process. The sacrificial line removal step 512 may involve etching minimal or no etching of components other than the sacrificial lines 606, 614, and 616.

Figure 19A:
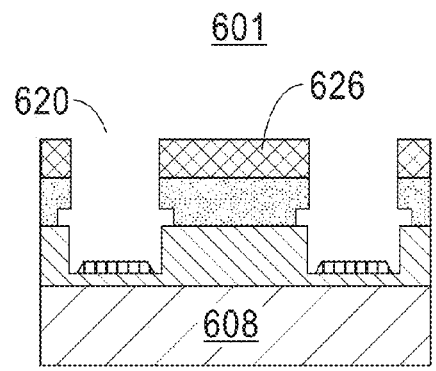
FIGS. 19A, 19B and 19C show cross-sectional views of the port region, nanochannel region and feed channel region, respectively, of a pinch off step, in accordance with the third example method for constructing a nanochannel sensor.
Figure 19B:
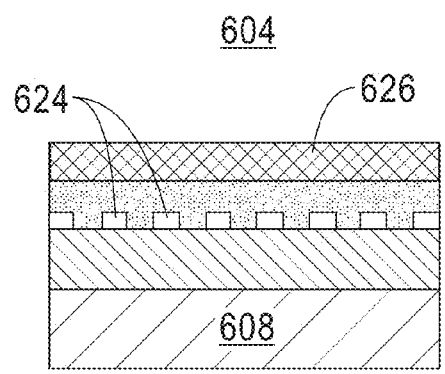
Figure 19C:
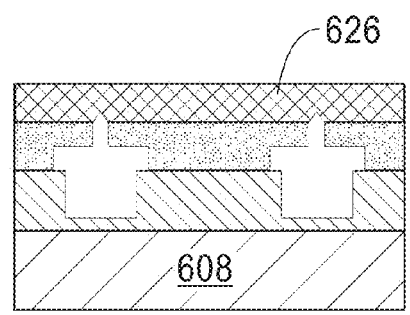

Returning to FIG. 12, after the sacrificial line removal step 512, the method 500 proceeds to a pinch-off step 514, as shown on FIGS. 19A-19C. At the pinch-off step 514, a pinch-off layer 626 is deposited on the capping layer 618. The pinch-off layer 626 may seal or "pinch off" the openings 609 over the feed channel region 602 but not pinch off the relatively larger opening 620 over the port region 601 leading to the sacrificial lines 606, 614, and 616. The pinch-off layer 626 may be a thin non-conformal insulator layer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of aligning electrodes to a nanochannel sensor, the method comprising:
    forming a sacrificial line on an insulating layer;
    forming a dielectric layer on the substrate and around the sacrificial line;
    etching at least one pair of electrode trenches in the dielectric layer on opposite sides of the sacrificial line;
    forming at least one pair of electrodes by filling the electrode trenches with electrode material; and
    removing the sacrificial line to form a nanochannel between the at least one pair of electrodes.

2. The method of claim 1, wherein etching at least one pair of electrode trenches in the dielectric layer also includes etching the dielectric layer at a faster etch rate than etching the first sacrificial line.

3. The method of claim 2, further comprising depositing a capping layer covering the sacrificial line and the electrodes.

4. The method of claim 3, further comprising forming a plurality of openings through the capping layer leading to the sacrificial line.

5. The method of claim 4, wherein the sacrificial line contains at least one of amorphous silicon, polysilicon, germanium, tungsten, molybdenum, tantalum and tantalum nitride.

6. The method of claim 5, wherein removing the sacrificial line to form a nanochannel includes introducing xenon difluoride to the sacrificial line through the plurality of openings.

7. The method of claim 6, further comprising depositing a conformal layer between the sacrificial line and the electrode trenches.

8. The method of claim 7, wherein forming a plurality of openings through the capping layer includes forming the plurality of openings in the conformal layer.

9. The method of claim 2, wherein the dielectric layer contains silicon dioxide.

* * * * *